US00PP35273P2

(12) United States Plant Patent
van Sambeek

(10) Patent No.: US PP35,273 P2
(45) Date of Patent: Jul. 18, 2023

(54) ***GAILLARDIA* PLANT NAMED 'DOGAILSPINMAN'**

(50) Latin Name: *Gaillardia aristata*
Varietal Denomination: Dogailspinman

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/991,491

(22) Filed: Nov. 21, 2022

(51) Int. Cl.
*A01H 5/02* (2018.01)
*A01H 6/14* (2018.01)

(52) U.S. Cl.
USPC ..... Plt./431
CPC ..... *A01H 6/14* (2018.05)

(58) Field of Classification Search
USPC ..... Plt./431
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Gaillardia* plant named 'Dogailspinman', characterized by its compact, upright and mounded plant habit; freely branching habit; dense and bushy habit; strong leaves that resist yellowing; early and freely flowering habit; single-type inflorescences; ligulate-shaped ray florets that are golden orange in color with emarginate apices; and good garden performance.

2 Drawing Sheets

Botanical designation: *Gaillardia aristata.*

Figure 1:
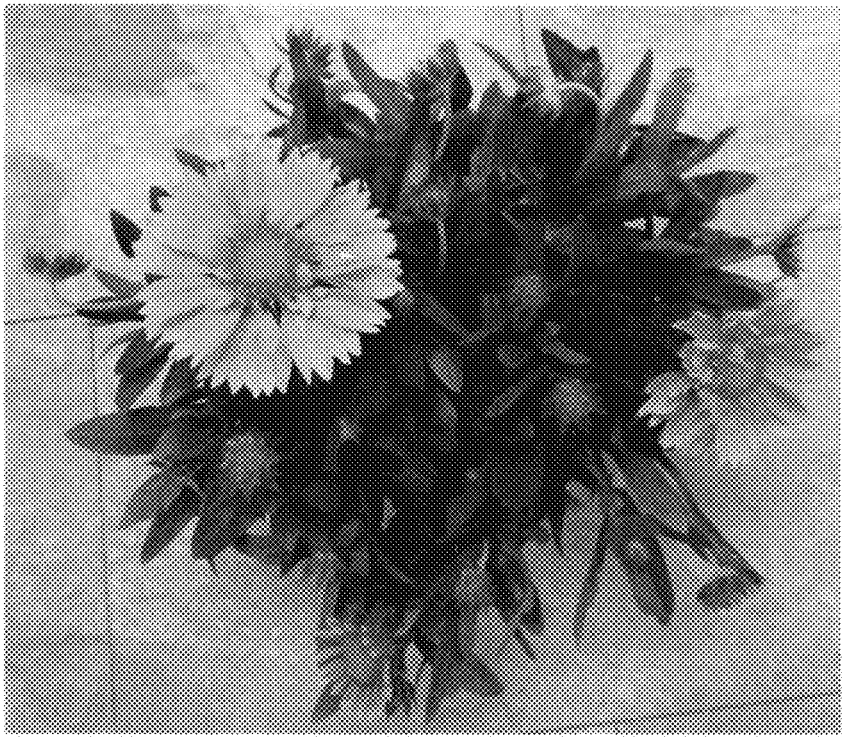

Cultivar denomination: 'DOGAILSPINMAN'.

CROSS-REFERENCED TO CLOSELY-RELATED APPLICATIONS

An European Community Plant Breeder's Rights application for the instant plant was filed by the Applicant/Assignee, Dümmen Group B.V. of De Lier, The Netherlands on Aug. 4, 2022, application number 2022/1838. Foreign priority is not claimed to this application.

BACKGROUND OF THE INVENTION

The present invention relates to a new and distinct cultivar of *Gaillardia* plant, botanically known as *Gaillardia aristata* and hereinafter referred to by the name 'Dogailspinman'.

The new *Gaillardia* plant is a product of a planned breeding program conducted by the Inventor in Aalsmeer, The Netherlands. The objective of the breeding program is to create new compact *Gaillardia* plants with unique and attractive inflorescences and healthy leaves.

The new *Gaillardia* plant originated from an open-pollination in July, 2016 of a proprietary selection of *Gaillardia aristata* identified as code number GA15-000036-004, not patented, as the female, or seed, parent with an unknown proprietary selection of *Gaillardia aristata* as the male, or pollen, parent. The new *Gaillardia* plant was discovered and selected by the Inventor as a single flowering plant from within the progeny of the stated open-pollination in a controlled environment in Aalsmeer, The Netherlands in July, 2017.

Asexual reproduction of the new *Gaillardia* plant by vegetative terminal cuttings in a controlled environment in Aalsmeer, The Netherlands, since August, 2017 has shown that the unique features of this new *Gaillardia* plant are stable and reproduced true to type in successive generations.

SUMMARY OF THE INVENTION

Plants of the new *Gaillardia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dogailspinman'. These characteristics in combination distinguish 'Dogailspinman' as a new and distinct *Gaillardia* plant:

1. Compact, upright and mounded plant habit.
2. Freely branching habit; dense and bushy habit.
3. Strong leaves that resist yellowing.
4. Early and freely flowering habit.
5. Single-type inflorescences.
6. Ligulate-shaped ray florets that are golden orange in color with emarginate apices.
7. Good garden performance.

Plants of the new *Gaillardia* differ primarily from plants of the female parent selection in ray floret color as plants of the new *Gaillardia* have golden orange-colored ray florets whereas plants of the female parent selection have yellow-colored ray florets.

Plants of the new *Gaillardia* can be compared to plants of *Gaillardia* x *grandiflora* 'Mesa Yellow', not patented. In side-by-side comparisons, plants of the new *Gaillardia* differ from plants of 'Mesa Yellow' in ray floret color as ray florets of plants of the new *Gaillardia* are golden orange in color whereas ray florets of plants of 'Mesa Yellow' are yellow in color.

Plants of the new *Gaillardia* also can be compared to plants of *Gaillardia* x *grandiflora* 'Mesa Peach', not patented. In side-by-side comparisons, plants of the new *Gaillardia* differ from plants of 'Mesa Peach' in ray floret color as ray florets of plants of the new *Gaillardia* are golden orange in color whereas ray florets of plants of 'Mesa Peach are yellow and orange bi-colored.

BRIEF DESCRIPTION OF THE PHOTOGRAPHS

The accompanying colored photographs illustrate the overall appearance of the new *Gaillardia* plant showing the colors as true as it is reasonably possible to obtain in colored reproductions of this type. Colors in the photographs may differ slightly from the color values cited in the detailed botanical description which accurately describe the colors of the new *Gaillardia* plant.

The photograph on the first sheet (FIG. 1) is a top perspective view of a typical flowering plant of 'Dogailspinman' grown in a container.

Figure 2:
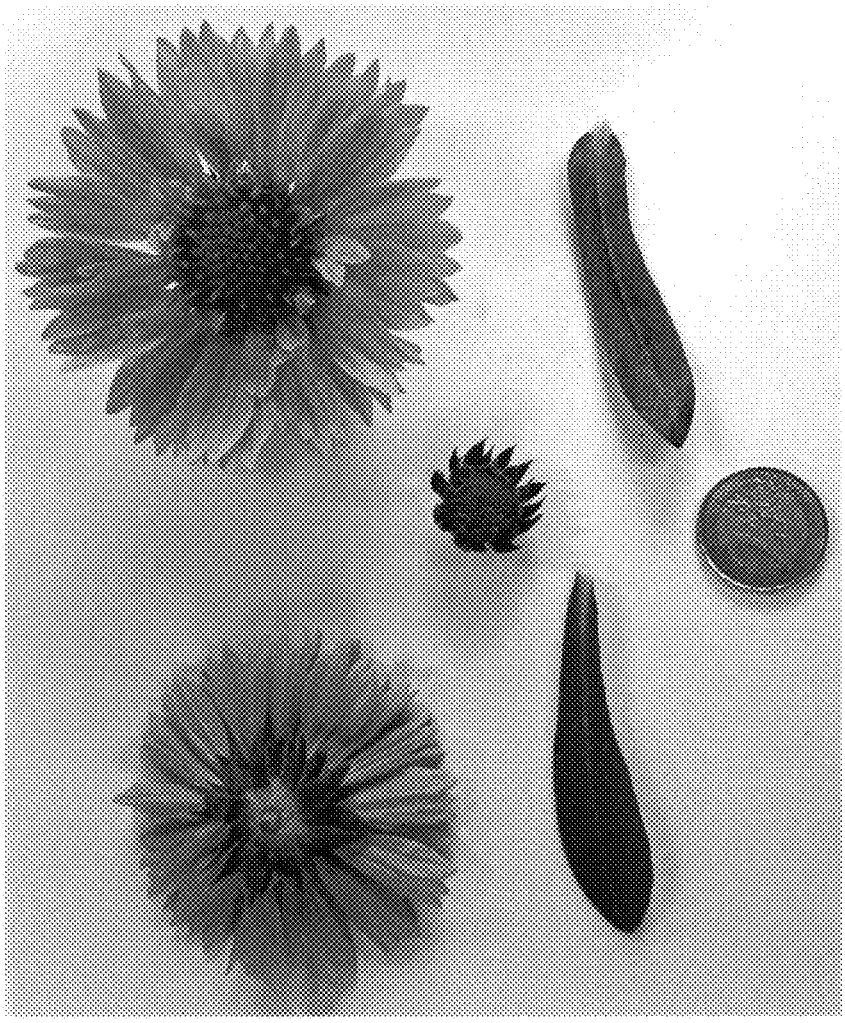

The photograph on the second sheet (FIG. 2) are close-up view of typical leaves, inflorescence buds and open inflorescences of 'Dogailspinman'.

DETAILED BOTANICAL DESCRIPTION

The aforementioned photograph and following observations and measurements describe plants grown in 13-cm containers during the summer in an outdoor nursery in Straelen, Germany and under cultural practices typical of commercial *Gaillardia* production. During the production of the plants, day temperatures averaged 22° C. and night temperatures averaged 17° C. Plants were pinched one week after planting and were 14 weeks old when the photographs and description were taken. In the following description, color references are made to The Royal Horticultural Society Colour Chart, Fifth Edition, except where general terms of ordinary dictionary significance are used.

Botanical classification: *Gaillardia aristata* 'Dogailspinman'.

Parentage:

*Female, or seed, parent.*—Proprietary selection of *Gaillardia aristata* identified as code number GA15-000036-004, not patented.

*Male, or pollen, parent.*—Unknown proprietary selection of *Gaillardia aristata*, not patented.

Propagation:

*Type.*—Terminal vegetative cuttings.

*Time to initiate roots, summer.*—About twelve days at temperatures about 26° C.

*Time to initiate roots, winter.*—About two weeks at temperatures about 23° C.

*Time to produce a rooted young plant, summer.*—About two weeks at temperatures about 23° C.

*Time to produce a rooted young plant, winter.*—About 16 days at temperatures about 18° C.

*Root description.*—Medium in thickness, fibrous; typically white to light brown in color, actual color of the roots is dependent on substrate composition, water quality, fertilizer type and formulation, substrate temperature and physiological age ofroots.

*Rooting habit.*—Moderately freely branching, medium density.

Plant description:

*Plant and growth habit.*—Herbaceous perennial; compact, upright and mounded plant habit; moderately vigorous growth habit and moderate growth rate; freely branching habit with about seven primary branches each with about seven secondary branches developing per plant; dense and bushy appearance.

*Plant height.*—About 21 cm.

*Plant width.*—About 34 cm.

*Lateral branch description.*—Length: About 19 cm. Diameter: About 1 cm. Internode length: About 5 mm. Strength: Strong. Aspect: Mostly upright. Texture and luster: Pubescent; glossy. Color, developing: Close to 145C. Color, developed: Close to 145B.

*Leaf description.*—Arrangement: Alternate, simple; sessile. Length: About 11 cm. Width: About 3 cm. Shape: Roughly lanceolate to linear. Apex: Acute. Base: Obtuse. Margin: Entire or occasionally with shallow lobes. Texture and luster, upper and lower surfaces: Pubescent, somewhat rough; semi-glossy. Venation pattern: Pinnate. Color: Developing leaves, upper and lower surfaces: Close to 146B. Fully developed leaves, upper surface: Close to 147B; venation, close to 147B. Fully developed leaves, lower surface: Close to 147C; venation, close to 147C.

Inflorescence description:

*Appearance.*—Single inflorescence form with ray and disc florets; inflorescences held mostly upright on strong peduncles; ray and disc florets develop acropetally on a capitulum.

*Fragrance.*—Faintly fragrant; pleasant.

*Flowering response.*—Plants begin flowering about ten weeks after planting; plants flower naturally during June and July in The Netherlands and Germany; inflorescences not persistent.

*Quantity of inflorescences.*—Freely flowering habit, about 119 inflorescences developing per plant during the flowering season.

*Inflorescence size.*—Diameter: About 9 cm. Height: About 2.5 cm. Disc diameter: About 3 cm.

*Receptacles.*—Height: About 3 mm. Diameter: About 1.4 cm. Shape: Button-shaped. Color: Close to 144D.

*Inflorescence buds.*—Height: About 1.3 cm. Diameter: About 2.2 cm. Shape: Button-shaped. Texture and luster: Smooth, glabrous; matte. Color: Close to 143A.

*Ray florets.*—Quantity per inflorescence: About 29 ray florets arranged in one to two whorls. Length: About 2.3 cm to 3.5 cm. Width: About 0.7 cm to 2 cm. Shape: Ligulate. Apex: Emarginate with about three acute apices. Base: Acuminate. Margin: Entire; not undulate. Aspect: Mostly horizontal. Texture and luster, upper surface: Smooth, glabrous; semi-glossy. Texture and luster, lower surface: Pubescent, slightly rough; glossy. Color: When opening, upper surface: Close to N25A; towards the apex, close to 17A. When opening, lower surface: Close to 26A; towards the apex, close to 17B. Fully opened, upper surface: Close to 26A; towards the apex, close to 17B; venation, similar to lamina colors; main color becoming closer to 26B with subsequent development. Fully opened, lower surface: Close to 26B; towards the apex, close to 17B; venation, close to 143A; color does not change with subsequent development.

*Disc florets.*—Quantity per inflorescence: About 106 massed at the center of the receptacle in about eight whorls. Length: About 1.4 cm. Diameter: About 3 mm. Shape: Fused tubular. Apex: Acuminate. Texture and luster, inner surface: Smooth, glabrous; semi-glossy. Texture and luster, outer surface: Pubescent; semi-glossy. Color: When opening, inner and outer surfaces: Close to 17A; towards the apex, close to N30A. Fully opened, inner and outer surfaces: Close to N30A.

*Involucral bracts.*—Quantity per inflorescence: About 31 arranged in about three whorls. Length: About 1.8 cm. Width: About 5 mm. Shape: Elliptic. Apex: Acuminate. Base: Truncate. Margin: Entire; ciliate. Texture and luster, upper and lower surfaces: Pubescent; semi-glossy. Color, upper and lower surfaces: Close to 143A.

*Peduncles.*—Length, terminal peduncle: About 6.5 cm. Diameter, terminal peduncle: About 3 mm. Length, third peduncle: About 3.5 cm. Diameter, third peduncle: About 2 mm. Strength: Strong. Aspect, terminal peduncle: Mostly erect. Aspect, third peduncle: About 10° from stem axis. Texture and luster: Smooth, glabrous; matte. Color: Close to 144D.

*Reproductive organs.*—Androecium: Present on disc florets only. Quantity per floret: Five. Filament length: About 4 mm. Filament color: Close to 145D. Anther size: About 1 mm by 6 mm. Anther shape: Rectangular with a pointed apex. Anther color: Close to 17A. Pollen amount: Abundant. Pollen color: Close to 17A. Gynoecium: Present on disc florets only. Quantity per floret: One. Pistil length: About 1.3 cm. Stigma diameter: About 6 mm. Stigma shape: Bi-fid. Stigma color: Close to N172A. Style length: About 7 mm. Style color: Close to 145B. Ovary color: Close to 145C.

*Seeds and fruits.*—To date, seed and fruit production have not been observed on plants of the new *Gaillardia.*

Pathogen & pest resistance: To date, plants of the new *Gaillardia* have not been observed to be resistant to pathogens and pests common to *Gaillardia* plants.

Garden performance: Plants of the new *Gaillardia* have been observed to have good garden performance and to tolerate wind and rain and temperatures ranging from about −30° C. to about 30° C. and to be suitable for U.S.D.A. Hardiness Zones 3 through 9.

It is claimed:

1. A new and distinct *Gaillardia* plant named 'Dogailspinman' as illustrated and described.

* * * * *